| United States Patent [19] | [11] Patent Number: 5,053,231 |
| Riffkin et al. | [45] Date of Patent: Oct. 1, 1991 |

[54] PROCESS FOR PREPARING AN ALCOHOLIC PRODUCT

[76] Inventors: Harry L. Riffkin, 22 Cramond Rd. S.; Thomas A. Bringhurst, 14B Double Hedges Park, James D. Gray, all of Edinburgh, Scotland

[21] Appl. No.: 318,455

[22] Filed: Mar. 2, 1989

Related U.S. Application Data

[63] Continuation of Ser. No. 918,157, Oct. 14, 1986, abandoned.

[30] Foreign Application Priority Data

Oct. 11, 1985 [GB] United Kingdom ............... 8525116

[51] Int. Cl.$^5$ ............................................... C12C 11/00
[52] U.S. Cl. .................................... 426/11.0; 536/124;
435/96; 435/99; 44/53
[58] Field of Search ........................ 536/1.1, 124, 99;
435/96; 426/11, 12

[56] References Cited

U.S. PATENT DOCUMENTS 3,868,307  2/1975  Von Laren ........................... 435/96
3,887,506  6/1975  Hewitt ............................... 260/17 A

OTHER PUBLICATIONS

The Merck Index., 9th ed., No. 7360, p. 985, 1976.

*Primary Examiner*—Elli Peselev
*Attorney, Agent, or Firm*—Anthony A. O'Brien

[57] ABSTRACT

Carbohydrate or material containing carbohydrate such as cereal, corn, rice, sorghum, potato and the like including Biomass and other sources of cellulose or non-fermentable sugars, is mixed with water and heated in the presence of a surfactant, typically a non-ionic detergent. The process may avoid the need for a subsequent pressure cooking step prior to fermentation to yield alcohol.

7 Claims, No Drawings

PROCESS FOR PREPARING AN ALCOHOLIC PRODUCT

This application is a continuing application based on a parent patent application Ser. No. 918,157 filed Oct. 14, 1986, now abandoned.

This invention is concerned with a process for treating "carbohydrate" as herein defined to render it susceptible to subsequent enzymic conversion to one or more fermentable sugars. The invention is principally directed to an improved method of processing carbohydrate source material wherein lower heating temperatures may be utilised.

Although it was previously accepted that carbohydrate was confined to naturally occurring substances corresponding to the formula—$(C.H_2O)_n$, the term "carbohydrate" is used in this specification to include polymeric carbohydrates and simpler carbohydrates. The term is therefore used to include the simple sugars, e.g. glucose, fructose, sucrose and maltose; reserve polymeric carbohydrates e.g. starch, cellulose, glycogen and laminarin; and complex hetero and substituted carbohydrates such as hemicelluloses, glycoproteins and the like.

Cereals or tubers are the preferred sources of reserve polymeric carbohydrate, mainly in the form of starch. Optionally, Biomass I may be used as a source of structural polymeric carbohydrate in the form of cellulose and hemicelluloses, and/or Biomass II may be utilized as a source of soluble, structural, reserve and transport sugars in the form of pectins, fructans and sucrose.

Sucrose as found in sugar cane may be deployed.

Generally sugar syrups are produced from sources of starch which are subjected to high temperature and high pressure cooking i.e. above 100° C., and followed by enzymic conversions to glucose and fructose prior to the fermentation process to yield alcohol.

BIOMASS e.g. cellulose, may be heat treated to extract the cellulose components, cooled and treated with fungal enzymes to reduce the cellulose to fermentable sugars which may then be fermented by yeast or other microbial systems. In general, BIOMASS relates to an organic material derived from plant sources whose major carbohydrate content is polymeric carbohydrate in the form of cellulose.

The present invention may be seen to provide a process for treating carbohydrate (or material containing carbohydrate), which renders it susceptible to subsequent conversion to fermentable sugar(s). Also the invention embraces fermentation processes utilizing treated carbohydrate and alcohol produced from such fermentations.

Cereal, corn, maize, rice and tuber (e.g. potato or cassava) starches are conventionally prepared for fermentation by mixing with water and then subjecting the resulting slurry to pressure cooking at a high temperature (approximately 145° C.). Cooking at such high temperature renders the starch susceptible to conversion to fermentable sugars by the enzyme system of malted cereals such as barley or by fungal enzymes. After conversion to fermentable sugars the product may be fermented by, e.g. microbial systems such as bacterial or yeast fermentations to obtain alcohol. The disadvantageous, high energy, high temperature treatment is essentially universal in the production of potable spirit for the alcoholic beverage industry and in the production of fuel ethanol, e.g. gasahol.

The high temperature treatment is a general prerequisite for treating starches from a variety of plant sources where enzymic conversion to soluble sugars is required, for example the production of glucose and fructose syrups for use in the food processing industry or in the reduction of BIOMASS in fermentation as used in the fuel industry. Comparatively high temperatures are also required for sparging as used in the infusion mashing system of malted cereals. High temperature sparging is a method of eluting soluble sugars from the malted cereal mash. Conventional sparging water temperatures may comprise primary sparging at 75° C., secondary sparging at 85° C. and tertiary sparging at 100° C.

Use of high temperatures within industry requires considerable energy input and it is desirable to reduce energy input for processes to make them economically and commercially more attractive.

It is from a consideration of the high temperature pressure cooking requirement of carbohydrate processing that has led to the present invention.

According to this invention there is provided a process for treating carbohydrate or material containing carbohydrate which comprises mixing the said carbohydrate or material with water and heating the mixture in the presence of a surfactant.

The treatment renders the carbohydrate capable of subsequent enzymic conversion to fermentable sugar(s). The treated carbohydrate may not require pressure cooking prior to enzymic conversion or, in the case of infusion mashing, further heat treatment may be restricted to temperatures below 80° C.

The carbohydrate may structurally comprise di- and/or oligo- and/or poly-saccharides as found in naturally occurring source material or mixtures thereof. The carbohydrate to be treated may comprise reserve polymeric carbohydrate such as, for example starch which may be extracted from materials already mentioned.

In accordance with the invention the heating of the mixture may be at a temperature in the range of 50°–95° C., preferably 60°–90° C., and more preferably at a temperature in the range of 60°–75° C.

The surfactant may comprise a detergent and the detergent may be a non-ionic variety. The concentration of surfactant in the mixture may be in the range of 0.01 to 10% v/v, preferably 0.01 to 6% v/v and more preferably in the range of 0.075 to 6% v/v.

The invention also includes within its scope sugar solutions such as syrups obtained directly by the method of treating carbohydrate.

We have found that when fermentable sugars are obtained by the present process, the subsequent yields of alcohol can approach the yields obtained by conventional higher temperature and/or pressure processing. It is therefore possible to produce ethanol by fermentation with considerable savings in energy costs whether that ethanol is required for the alcoholic beverage industry or other industrial requirements. The present process, when applied to the infusion mashing system of malted cereals can result in significant savings in energy costs in the production of sugar syrups as currently used by the food processing industry.

The present process can therefore provide considerable savings in production costs where reserve carbohydrate such as starch is a major component of the source material employed and where hot water extraction techniques form at least one step in their treatment towards obtaining fermentable sugars.

In particular it has been found that pressure cooking of carbohydrate such as cereal, corn, maize, rice and tuber starches in slurry form can be avoided. The present process can be applied to these source materials at temperatures below the boiling point of water. It has been surprisingly found that this is possible by the addition of a surfactant.

In order that the invention may be further illustrated and readily carried into effect, embodiments thereof will now be described by way of example only.

EXAMPLE 1

Wheat

Whole wheat was ground (Miag mill setting 2) and preslurried at 68° C. for one hour with the inclusion of Triton X100 at 0.1% v/v in the slurry water.

Following the slurry treatment the temperature was reduced to 63° C. and mashing was initiated by the addition of barley malt.

After one hour the mash was cooled to 25° C. and transferred to a fermenting flask with inoculation by a strain of

*Saccharomyces cerevisiae.*

On completion of fermentation the ethanol was distilled and quantified.

Results showed a spirit yield of 435.7 liters of alcohol per tonne of wheat on a dry weight basis.

This compared with a yield of 435.4 liters of alcohol per tonne when the same wheat was subjected to high temperature pressure cooking at 145° C.

Thus the results showed that equivalent yields of alcohol could be obtained at the lower temperature when the surfactant was included.

EXAMPLE 2

Malted Cereal (Barley)

Infusion mashing involves the mixing of malted cereals with hot water at around 63° C. and then allowing the resultant mash to infuse for approximately one hour. During this time the process of saccharification occurs and the resultant soluble sugars are then removed from the mash by first draining and then by high temperature sparging (eluting).

A second experiment involved using the surfactant in a conventional infusion mash using 100% barley malt.

Mashing was at 63° C. followed by three 75° C. sparges.

The control experiment utilised conventional sparging at 75° C., 85° C. and 100° C. respectively.

The results showed the lower temperature regime with the inclusion of the surfactant gave a yield corresponding to 99.2% of that of the control.

The surfactant used was Triton X100 at a concentration of 0.1% v/v in the mashing and sparge water.

EXAMPLE 3

Brown Rice

Brown rice (circa 35 g) was ground in a Miag mill (setting 0.2 mm) and a representative sample of the resultant grits weighed accurately to 30.0006 g. The sample was then slurried with cold water (81 ml) and subjected to pressure cooking at 145° C. for circa 60 minutes. On completion of the cook the slurry was cooled to 65° C. and mashed with malt grist slurry, composed of malt grist (7.0346 g) and water (50 ml), for one hour. The resultant mash was transferred to a 500 ml round bottomed flask, made up to 250 ml with distilled water and cooled to 25° C. before pitching with DCL 'M' type yeast (1 g). The pitched wort was then fermented at 30°-32.2° C. On completion of fermentation the wash was distilled and estimated for alcohol content. The calculated yield of alcohol (ethanol) based on the dry weight of rice grits was measured at 498.21 LA tonne$^{-1}$ (liters of alcohol per tonne).

Similar ratios of ground brown rice and malt were prepared for fermentation except that the pressure cooling was omitted and instead the brown rice slurry was treated by heating at 68° C. for one hour both in the absence and presence of Triton X 100 at a concentration of 0.1% v/v. Following the low temperature processing the slurry was cooled to 65° C. and mashed, fermented and distilled as previously described for the conventional cook.

The resultant yields of alcohol were 511.93 LA tonne$^{-1}$ in the absence of the surfactant and 518.02 LA tonne$^{-1}$ in the presence of the surfactant, the latter giving a yield improvement of 4% on the pressure cooked sample without the energy input of processing at 145° C.

EXAMPLE 4

Potato

Whole potatoes (2 kg) were washed free of adhering soil, cut up into small cubes and dried to a moisture content of circa 11%. The dried cubes were then ground in a laboratory mill and reground to a Miag mill setting of 0.2 mm. The grits were then processed, mashed, fermented and distilled as described for the brown rice experiments. The results were as follows:

Pressure cooked control: 435.49 LA tonne$^{-1}$
68° C. slurry: 430.87 LA tonne$^{-1}$
68° C. slurry+TX100: 437.29 LA tonne$^{-1}$ These results show a yield advantage for the surfactant treated, low temperature processed sample of 0.4% over the high temperature cooked control and even higher over slurry in the absence of surfactant.

EXAMPLE 5

Sorghum

Sorghum grits were processed in the same manner as for the brown rice experiment except that for the low temperature processing a second stand at 85° C. for 20 minutes followed the initial 60 minute slurry at 68° C. Thereafter the slurry was cooled to 65° C. and mashed as previously described. The results from the subsequent fermentations and distillations are shown below:

Pressure cooked control: 487.28 LA tonne$^{-1}$
68°/85° C. slurry: 452.07 LA tonne$^{-1}$
68°/85° C. slurry+TX100: 461.81 LA tonne$^{-1}$ While the low temperature slurry plus the surfactant only came within 5% of the control there was still a 2% improvement over the low temperature slurry without the added surfactant. While these results failed to meet the control yield they show quite clearly that a considerable improvement was possible using the surfactant and it may be that a modification in the low temperature regime will give better results.

EXAMPLE 6

Maize

Ground maize was processed in a similar manner to the brown rice except that (a) the slurry temperature was 75° C. and (b) 25% of the malt grist was added during the work up to 85° C. The results are shown below:

Cooked control: 454.62 LA tonne$^{-1}$
85° C.: 431.41 LA tonne$^{-1}$
85° C.+TX100: 439.93 LA tonne$^{-1}$
85° C.+malt: 446.11 LA tonne$^{-1}$
85° C.+malt+TX100: 449.98 LA tonne$^{-1}$ A consistent improvement using the surfactant was obtained and when this was utilised in conjunction with the pre-malting step the yield obtained was within 1% of the cooked control.

The data obtained from our examples on rice, potato, sorghum, maize and what, clearly demonstrate a significant commercial/economic and unexpected advantage can be obtained by using a surfactant in carbohydrate processing for fermentation.

The following examples illustrate the process using a variety of commercially available sufactants. Each employed wheat as the material containing carbohydrate and were processed in similar fashion to the procedure of example 1, using similar volumetric percentages of the different surfactants, but minor variation of temperature or processing time therefrom. The parameters used for all these subsequent examples were nevertheless kept constant as far as experimentally possible.

COMPARATIVE CONTROL EXAMPLE 7

Surfactant Absent, Non-Pressure Cooked

Following procedure based on example 1 but in the absence of surfactant, a spirit yield of 409.88 LA tonne$^{-1}$ was obtained from the treated wheat on a dry weight basis. A yield of 412 or more in the presence of surfactant may be regarded as significant, although any increase is an improvement.

COMPARATIVE CONTROL EXAMPLE 8

Surfactant Absent, Pressure Cooked at 145° C.

Example 7 was repeated but before fermentation, the treated wheat slurry was pressure cooked at 145° C. The yield of alcohol increased to 425.26 LA tonne$^{-1}$ (on the same basis) and provides a target figure for examples using surfactant but not pressure cooking to approach. TABLE 1 below lists the sufactants and results obtained from examples 9-22 inclusive. All represent significant and unexpected improvement over control example 7 and some approach the yield of control example 8.

TABLE 1

| Example | Surfactant (trademark) | Type | Generic Class | Specific composition | Alcohol Yield from treated wheat (L A tonne −1) |
|---|---|---|---|---|---|
| 9 | Span 80 | non-ionic | unethoxylated sorbitan fatty acid ester | Sorbitan mono oleate | 412.18 |
| 10 | — | non-ionic, detergent | ethoxylated alkyl ether | polyoxyethylene (20) cetyl ether | 412.18 |
| 11 | Triton X-305 | non-ionic, detergent | ethoxylated (alkyl) phenol | polyoxyethylene (30) p-t-octylphenol | 412.18 |
| 12 | Tyloxapol | non-ionic, detergent | ethoxylated (aromatic) phenol | p-iso-octylpolyoxyethylene phenol formaldehyde polymer | 413.72 |
| 13 | Tween 20 | non-ionic | ethoxylated sorbitan fatty acid ester | polyoxyethylene (20) sorbitan monolaurate | 415.25 |
| 14 | — | non-ionic, detergent | ethoxylated alkyl ether | polyoxyethylene (23) lauryl ether | 415.25 |
| 15 | Tween 80 | non-ionic | ethoxylated sorbitan fatty acid ester | polyoxyethylene (20) sorbitan mono oleate | 416.79 |
| 16 | — | non-ionic, detergent | ethoxylated alkyl ether | polyoxyethylene (10) cetyl ether | 416.79 |
| 17 | Nonidet P 40 | non-ionic, detergent | ethoxylated (alkyl) phenol | polyoxyethylene (9) p-t-octylphenol | 416.81 |
| 18 | Triton X-45 | non-ionic, detergent | ethoxylated (alkyl) phenol | polyoxyethylene (5) p-t-octylphenol | 418.34 |
| 19 | Span 20 | non-ionic | unethoxylated sorbitan fatty acid ester | sorbitan monolaurate | 420.64 |
| 20 | Span 60 | non-ionic | unethoxylated sorbitan fatty acid ester | sorbitan monostearate | 420.64 |
| 21 | Triton X-100 | non-ionic, detergent | ethoxylated (alkyl) phenol | polyoxyethylene (9-10) p-t-octylphenol | 421.41 |
| 22 | Lubrol PX | non-ionic, detergent | ethoxylated alcohol | polyoxyethylene (9-10) lauryl-myristyl alcohol | 421.42 |

We claim:

1. A process for preparing an alcoholic product wherein the improvement comprises mixing carbohydrate or material containing carbohydrate with water, heating the mixture to 50°-95° C. in the presence of a surfactant selected from the group consisting of non-ionic detergents prior to the enzymatic conversion of said carbohydrate or material containing carbohydrate to a fermentable sugar and fermenting the said sugar to yield an alcoholic product.

2. A process as claimed in claim 1, wherein prior to fermentation the mixture is heated to 60°-90° C., and not pressure cooked.

3. A process as claimed in claim 1, in which the concentration of surfactant in the mixture is 0.01 to 10% v/v.

4. A process as claimed in claim 1, in which the concentration of surfactant in the mixture is 0.01 to 6% v/v.

5. A process as claimed in claim 1, in which the carbohydrate or material containing carbohydrates selected from the group consisting of: cereal, malted cereal, corn, maize, wheat, rice, sorghum, potato, cassave, cellulose, hemicellulose and sugar(s).

6. A process as claimed in claim 1, wherein the carbohydrate is a malted cereal.

7. A process as claimed in claim 6, wherein the malted cereal is subjected to a sparging process.

* * * * *